United States Patent
Ponzini

(10) Patent No.: US 7,311,023 B2
(45) Date of Patent: Dec. 25, 2007

(54) REPLACEABLE-HEAD DENTAL CARE TOOL WITH IMPROVED ENGAGEMENT THEREOF

(75) Inventor: Eligio Ponzini, Lazzate (IT)

(73) Assignee: Ponzini S.p.A., Lazzate (Milan) (IT)

( * ) Notice: Subject to any disclaimer, the term of this patent is extended or adjusted under 35 U.S.C. 154(b) by 0 days.

(21) Appl. No.: 11/485,437

(22) Filed: Jul. 13, 2006

(65) Prior Publication Data

US 2007/0017545 A1  Jan. 25, 2007

(30) Foreign Application Priority Data

Jul. 14, 2005   (IT)   ................... MI200500259 U

(51) Int. Cl.
| B25B 16/23 | (2006.01) |
| B25G 1/00 | (2006.01) |
| A61C 3/00 | (2006.01) |
| A61C 1/08 | (2006.01) |
| A45C 3/00 | (2006.01) |
| A45C 7/00 | (2006.01) |
| A45C 13/22 | (2006.01) |
| A45C 13/26 | (2006.01) |
| A45C 5/10 | (2006.01) |

(52) U.S. Cl. ............... 81/177.1; 443/146; 443/126; 16/422

(58) Field of Classification Search .......... 81/62, 81/60, 177.1; 15/167.1, 143.1, 145, 176.1, 15/176.6, 111, 206; 433/146–147, 126; 132/322–329; 16/422, 111, 206

See application file for complete search history.

(56) References Cited

U.S. PATENT DOCUMENTS

| 3,072,938 | A | * | 1/1963 | Phaneuf ................ 15/22.1 |
| 4,771,148 | A | * | 9/1988 | Bersonnet ........ 200/61.58 R |
| 4,850,735 | A | * | 7/1989 | Hansen et al. ........... 403/330 |
| 5,346,324 | A | * | 9/1994 | Kuo ...................... 401/146 |
| 5,511,276 | A | * | 4/1996 | Lee ...................... 15/167.1 |
| 5,682,641 | A | * | 11/1997 | Newman et al. .......... 16/429 |
| 5,840,013 | A | * | 11/1998 | Lee et al. ................. 600/114 |
| 5,875,796 | A | * | 3/1999 | Silver-Isenstadt et al. .. 132/311 |
| 5,934,295 | A | * | 8/1999 | Gekhter et al. .......... 132/309 |
| 6,145,152 | A | * | 11/2000 | Ward ..................... 15/176.1 |
| 6,546,585 | B1 | * | 4/2003 | Blaustein et al. ......... 15/167.1 |
| 6,558,402 | B1 | * | 5/2003 | Chelak et al. ............ 606/182 |
| 2004/0068809 | A1 | * | 4/2004 | Weng ..................... 15/22.1 |

\* cited by examiner

*Primary Examiner*—Alvin J. Grant
(74) *Attorney, Agent, or Firm*—Young & Thompson

(57) ABSTRACT

A replaceable-head, dental care tool is disclosed, of the type including a handle element (1) and a tool element, the tool element including an engaging extension (10) having at least one flexible reed element (11) equipped with an end pawl (12), and the handle element comprising an engagement seat (2) for the engaging extension (10) which has a shoulder (2b') able to retain the pawl (12), as well as an activation button (5) in the shape of a separate button and capable of pushing on the pawl (12) to disengage it from the shoulder (2b'), the seat (2) being externally surrounded by an edge (4) of soft elastic material wherein the button (5) is circumferentially enclosed.

8 Claims, 5 Drawing Sheets

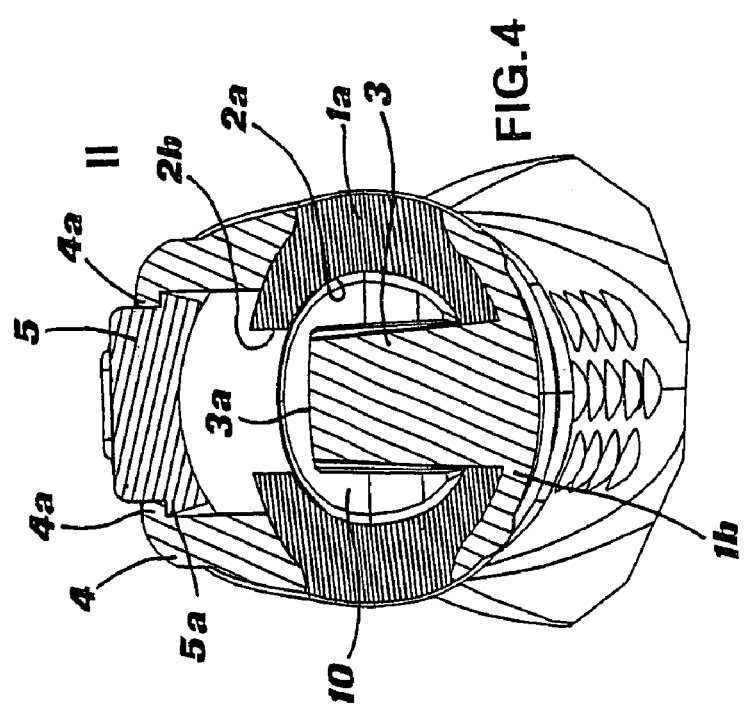

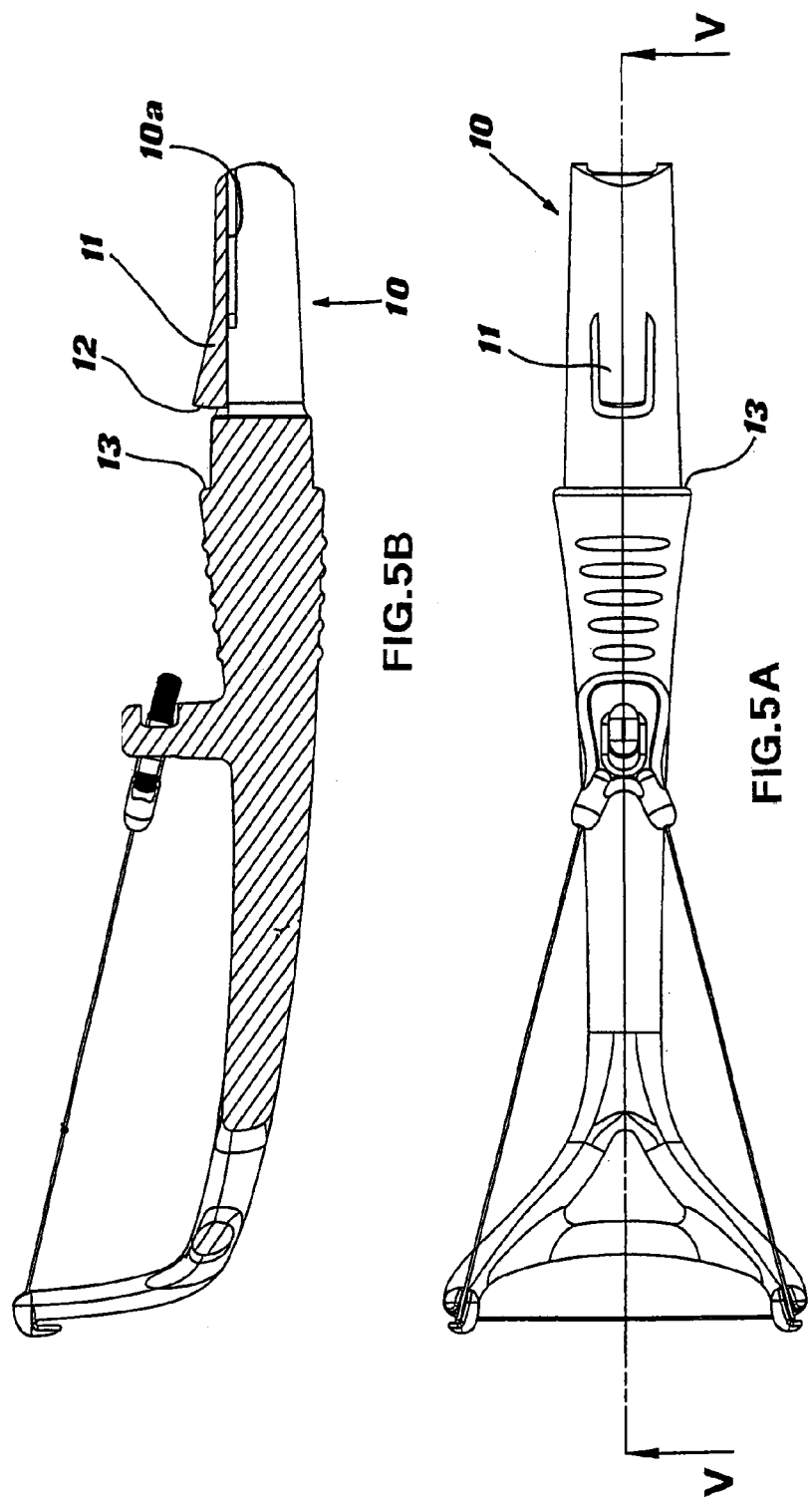

REPLACEABLE-HEAD DENTAL CARE TOOL WITH IMPROVED ENGAGEMENT THEREOF

The present invention concerns a dental care tool with a replaceable active portion. In particular, it concerns a dental care tool which may be disassembled into a handle element and a replaceable active tool element, equipped with an improved engaging and locking system.

As known, brushes with a replaceable bristled-in portion have existed on the market for some time, designed for the essential purpose of offering an oral hygiene device which exhibits appreciable environmental, economic and practical features.

At present, many types of these replaceable-head brushes exist, wherein the replaceable portion takes on correspondingly varying shapes and the assembly/disassembly whereof is easy and accurate to a varying degree.

One of these brushes is for example the one shown in international application WO01/87112 in the same Applicant's name—the content of which is here incorporated as a reference —according to which the preamble of the enclosed main claim is drafted.

This brush has proved very useful as a general concept, but has shown margins for improvement.

In particular it has been noticed that the activation button has construction limits which make it awkward to push and little effective when disengaging the head. Moreover, the head locking system in the handle is susceptible of improvement, since it is unable to provide high resistance to disengagement, especially if toothpaste residues build up over time and the plastic material tends to lose elasticity.

Moreover, the problem is particularly felt if assembly and disassembly of the dental tool and the handle occur frequently, for example whenever various interchangeable dental care items are mounted on the handle, as shown for example in U.S. Pat. No. 5,253,948 or in another application filed simultaneously in the same Applicant's name.

It is hence an object of the present invention to provide an improved dental care tool which may be disassembled, wherein the interchangeable tool may be securely assembled and locked to the handle, even following continued use.

Such object is perfectly achieved by a dental care tool equipped with an engagement system as described in its essential features in the accompanying claims.

According to a first aspect of the invention, it is provided a replaceable-head dental care tool, of the type comprising a handle element and a tool element, said tool element comprising an engaging extension having at least one flexible reed element equipped with an end pawl, and said handle element comprising an engagement seat for said engaging extension which has a shoulder able to retain said pawl, as well as an activation button belonging to the handle and capable of pushing on the pawl to disengage it from said shoulder, wherein said button is shaped as a separate button, said seat has an opening towards the button, externally surrounded by a rim of a soft elastic material circumferentially enclosing said button and wherein said button has at least one transversal projection towards the inside of the opening and capable of coming in contact with the pawl of the flexible reed when pressure is imparted thereon deforming part of said elastic rim.

Said rim is preferably provided with a lip retaining the button along a peripheral short rib thereof.

According to another aspect, said rim is further extended into a supporting block which partly occupies said opening and whereon the button is cantilever mounted. Said button has a rear pin engaged with the supporting block.

According to another aspect of the invention, said projection of the button is shaped as a front pin.

According to another inventive aspect, said seat comprises, below the button, a column of a soft elastic material which projects from the base of the seat and ends at a certain distance from the vault of the seat, the top head surface of the column being intended to oppose engaging extension and being arranged so as to oppose a progressively stronger elastic reaction upon progressive engagement of the extension withing the seat.

Further details on the features and advantages of the device according to the invention will in any case be more evident from the following description, given by way of example and shown in the accompanying drawings, wherein:

FIG. 4 is an enlarged cross-section view according to line IV-IV of FIG. 2; and

FIGS. 5A and 5B are top-plan and longitudinal cross-section views along line V-V, respectively, of a tool for the handle of FIG. 1.

Figure 1:
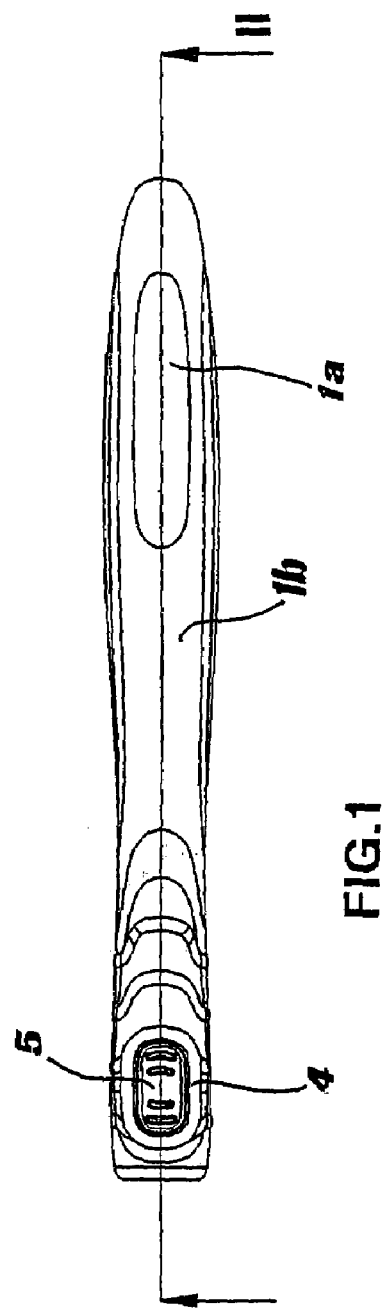
FIG. 1 is a top plan view of a handle according to the invention.
Figure 2:
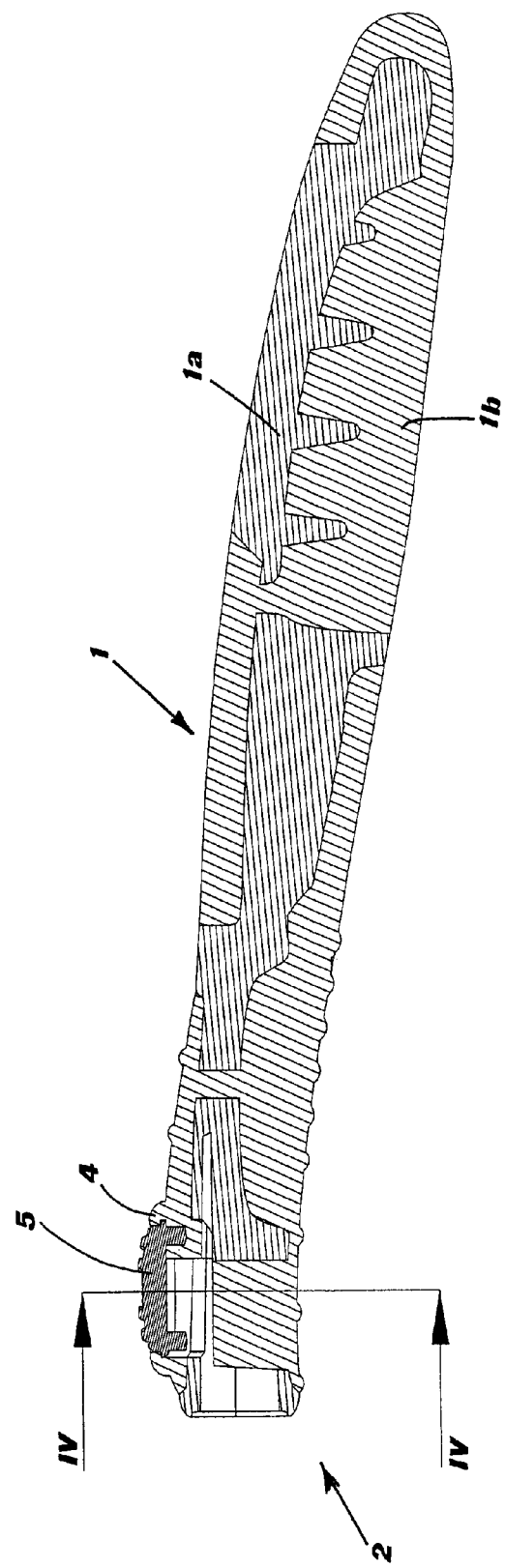
FIG. 2 is a cross-section view along line II-II of FIG. 1.
Figure 3:
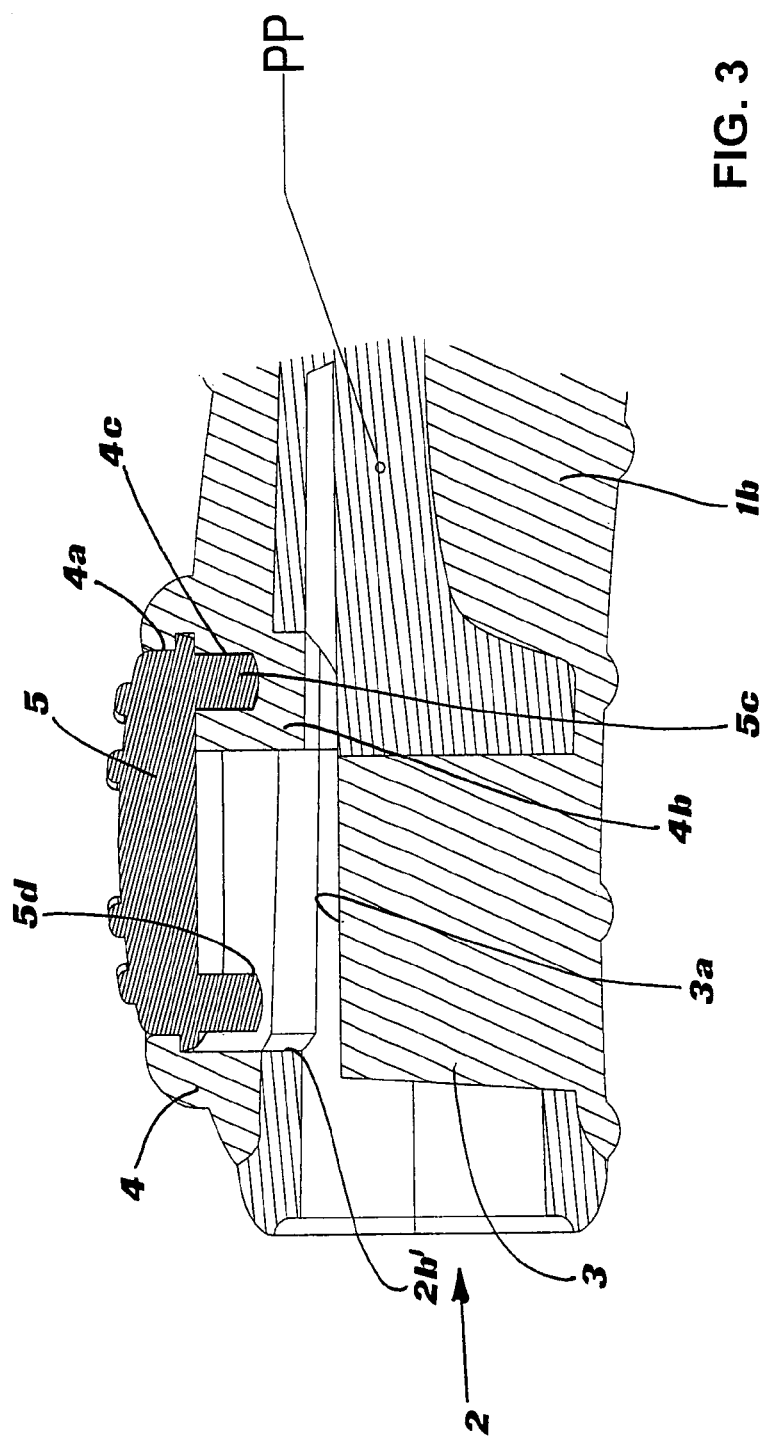
FIG. 3 is an enlarged view of a detail of FIG. 2.

A handle 1 of a dental care tool consists, in a manner known per se, of a structural frame 1a, for example made of polypropylene, co-moulded with a soft finish material 1b, such as an elastomeric material.

In the front part of the handle, a housing seat 2 for an engaging extension of a dental care tool is provided, which may be coupled with the handle. Said seat is provided within the handle and having a main axis substantially parallel to the axis of the handle.

In FIGS. 5A and 5B a bow tool with a floss is shown in an exemplificative way, which may be coupled with handle 1. Such tool is suitably equipped with an engaging extension 10, which shows a generically C-shaped section, on the back whereof a flexible reed 11 is provided, equipped with a pawl 12. The root end of the reed is connected to the distal end of the extension 10, while the displaceable end—equipped with the pawl 12—is closer to the active tool (see FIG. 5B).

The engaging extension 10 further ends with a shoulder relief 13, capable of abutting with the mouth of the seat 2 of handle 1 and hence of determining the end-stop position of extension 10 within the recess/seat 2. The shoulder relief 13 is preferably part of the same active portion of the tool.

The active portion of the tool will not be described in further detail, as it is the subject of separate applications filed simultaneously.

The seat 2 in handle 1 is formed as a hollow sized so as to house by precision the engaging extension 10. In particular, hollow 2 is defined by side walls 2a of the same structural material 1a as the handle and has a C-shaped profile substantially matching that of the engaging extension 10 of the dental care tool.

On the upper side (in the orientation of FIG. 4), i.e. on the vault of hollow 2, a through-opening 2b is provided, the usefulness whereof will be highlighted in the following. The front edge 2b' of such opening 2b is a shoulder against which pawl 12 of reed 11 is intended to set, when engaging extension 10 is fully inserted in its seat 2. In other words, when the tool is coupled in its operating position with is corresponding handle, pawl 12 abuts against shoulder 2b' while shoulder relief 13 abuts against the mouth of seat 2, which determines a full and tight locking of the tool on the handle.

From the lower part of the handle (in the orientation of FIG. 4) a column of elastomeric material 3 further projects towards the inside of hollow 2. This column is located, in a longitudinal direction, in correspondence of the area where reed 11 lyes when engaging extension 10 is fully inserted in seat 2.

Advantageously, column 3 is taller than the height of the hollow defined by the C-shaped profile of extension 10; therefore, introduction of extension 10 into its seat 2 may occur only by elastically deforming (by compression) column 3: the resulting elastic reaction of the column is further capable of pushing upwards the above-lying reed 11, so as to keep it actively pushed into opening 2b, with pawl 12 securely engaged with edge 2b', resulting in a firm engagement.

Moreover, the length of the column, in the direction of the depth of seat 2, is preferably such that it must be partly deformed also in this direction during introduction of extension 10.

This implies twofold results. As a matter of fact, on the one hand the user must make a progressively greater effort to couple the tool with the handle, up until pawl 12 snaps beyond shoulder 2b': this contributes to better signal to the user that the engagement end-stop has been reached (with a typical snap which may be felt as well as heard), with a diminished risk that the coupling may not be completed correctly and hence that the two members may accidentally become detached.

Secondly, this opposite elastic reaction aids self-expulsion of the tool from the handle when pawl 12 is released from shoulder 2b', according to the way shown further on. This self-expulsion feature contributes to making the device appealing to the user.

According to a preferred embodiment the invention, the upper head 3a of column 3 does not run perfectly parallel to the opposite bottom surface 10a of the C-shaped profile of extension 10. On the contrary, the head surface 3a is such that, as extension 10 is introduced into its seat 2, the elastic reaction deforming the column becomes progressively stronger. In particular, by proceeding towards the bottom of hollow 2, the top head surface 3a has a slope converging towards the bottom surface 10a of the C-shaped profile of extension 10.

This particular configuration contributes to the effect illustrated above.

Advantageously, on the coupling extension 10 a short wedge projection (not shown) is further provided, capable of entering a corresponding wedge recess provided in the wall at the mouth of seat 2. This wedge projection allows to univocally axially couple the two components—hence with a centring function—but it also has two further important functions. As a matter of fact, the wedge recess creates a bevel inlet which eases the introduction of the pawl of the flexible reed into seat 2. The same recess, allowing space for the pawl, immediately releases the elastic tension into the flexible reed when it is just outside the engagement with its seat: thereby friction between pawl 12 and the vault of seat 2 is greatly reduced and expulsion of the component is hence swifter and smoother.

According to the invention, opening 2b is further fully surrounded, on its outer side, by a raised rim 4 of elastomeric material.

Rim 4 houses and retains a button 5 of a more rigid material, for example plastic such as polypropylene. For such purpose, edge 4 is shaped so as to have a perimeter lip 4a defining an undercut under which a short rib 5a of button 5 remains engaged.

In the rear part, the elastomeric-material partly extends also with the opening 2b, defining a supporting block 4b wherein a constraint hole 4c is obtained. Button 5 correspondingly has a rear pin 5c, capable of entering hole 4c with interference.

Button 5 further has a front pin 5d, which is apt to lye exactly above the pawl 12 of reed 11.

Advantageously, button 5 is fully symmetrical about its main axes, hence the two pins 5c and 5d are perfectly equivalent and the button may be engaged with rim 4 in either one of two opposite positions offset by 180°.

In operation, button 5 is coupled with and housed in the rim 4, after having completed moulding of the handle, hence exploiting the elastic deformability of elastomeric rim 4. Engagement of pin 5c with hole 4c of block 4b results in the button to be cantilevered on the elastomeric block 4b, ensuring excellent elasticity and flexibility of the button under a finger's pressure.

Consequently, a slight pressure above the button may cause prompt yielding of the front part of button 5, with a rotation substantially about the point of engagement on elastomeric block 4b: this brings pin 5d to abut against the below-lying pawl 12, which is thereby lowered—overcoming the opposing elastic action of column 3—until it is disengaged from shoulder 2b'. In this condition, due to the specific configuration of the invention and without requiring simultaneous traction on the tool, automatic partial expulsion of extension 10 from its seat 2 is obtained, so much so that natural engagement of pawl 12 with shoulder 2b' is not allowed again upon release of button 5. Once a slight expulsion is determined, the tool may then be easily and fully uncoupled from the handle removing it.

As can be understood, operation of the engaging system according to the invention is efficient and intuitive.

Moreover, due to the separate manufacture of button 5 for later application, its shape and size may be better adapted to the requirements of ergonomics and ease of use.

Finally, the presence of the rim 4 made of yielding elastomeric material, wherein the perimeter of button 5 remains well embedded, allows to obtain a perfect seal, which prevents the formation of a gap wherein foreign substances deposit, such as scale or residues of cleaning agents (for example toothpaste), which are unappealing and affect operation of said button.

The improved engaging system suggested here hence solves the problems of the prior art, allowing the provision of an extremely effective, disengageable dental care tool which appeals to the user.

It is understood, however, that protection of the above-described invention is not limited to the specific embodiment shown, but extends to any other equivalent embodiment falling withint the scope of the attached claims.

For example, the position of button 5 may be chosen according to various criteria, for example it may also be arranged sideways to the handle or underneath the same, or multiple buttons may even be provided simultaneously.

The invention claimed is:

1. Replaceable-head dental care tool, of the type comprising a handle element (1) and a tool element, said tool element comprising an engaging extension (10) having at least one flexible reed element (11) equipped with an end pawl (12), and said handle element comprising an engagement seat (2) for said engaging extension (10) which has a shoulder (2b') able to retain said pawl (12), as well as an activation button (5) belonging to the handle and capable of pushing on the pawl (12) to disengage said pawl from said shoulder (2b'), characterised in that said button is shaped as a separate button (5), said seat (2) has an opening (2b) towards the button (5), externally surrounded by a rim (4) of a soft elastic material wherein said button (5) is circumferentially enclosed and in that said button (5) has at least one projection (5d) towards the inside of the opening (2b) and capable of coming in contact with the pawl (12) of the flexible reed (11) when pressure is imparted thereon deforming part of said elastic rim (4), and wherein said rim (4) further comprises a supporting block (4b) which partly occupies said opening (2b) and whereon the button (5) is cantilever mounted.

2. Dental care tool as in claim 1, wherein said rim (4) has a lip (4a) retaining the button (5) along a peripheral short rib (5A) thereof.

3. Dental care tool as in claim 1, wherein said button (5) has a rear pin (5c) engaged with said supporting block (4b).

4. Dental care tool as in claim 1, wherein said projection (5d) is shaped as a front pin.

5. Dental care tool as in claim 4, wherein said button (5) is symmetrical.

6. Dental care tool as in claim 1, wherein said seat (2) comprises, below the button (5), a column of a soft elastic material (3) which projects from the base of the seat (2) and ends at a certain distance from the vault of the seat (2).

7. Dental care tool as in claim 6, wherein the top head surface (3a) of said column (3) is intended to oppose engaging extension (10) and is arranged so as to oppose a progressively stronger elastic reaction upon progressive engagement of the extension (10) within the seat (2).

8. Dental care tool as in claim 1, wherein said soft elastic material is an elastomeric material.

* * * * *